United States Patent
Centanni et al.

(10) Patent No.: US 6,916,445 B2
(45) Date of Patent: Jul. 12, 2005

(54) SYSTEM AND METHOD FOR DECONTAMINATING ARTICLES

(75) Inventors: Michael A. Centanni, Parma, OH (US); Mark Kusner, Gates Mills, OH (US)

(73) Assignee: STERIS Inc., Temecula, CA (US)

( * ) Notice: Subject to any disclaimer, the term of this patent is extended or adjusted under 35 U.S.C. 154(b) by 412 days.

(21) Appl. No.: 10/305,606

(22) Filed: Nov. 27, 2002

(65) Prior Publication Data

US 2004/0101435 A1 May 27, 2004

(51) Int. Cl.[7] .................................................. A61L 2/00
(52) U.S. Cl. ..................... 422/22; 62/264; 62/311; 62/374; 422/1; 422/3; 422/23; 422/25; 422/186.05; 422/292; 422/293
(58) Field of Search ........................ 422/1, 3, 22, 23, 422/25, 40, 186, 186.05, 292, 293, 300; 62/259.1, 264, 311, 374

(56) References Cited

U.S. PATENT DOCUMENTS

| | | | | |
|---|---|---|---|---|
| 4,014,158 A | * | 3/1977 | Rausing | 53/167 |
| 4,620,962 A | * | 11/1986 | Brodbeck | 422/24 |
| 5,554,856 A | * | 9/1996 | Bidnyy et al. | 250/455.11 |
| 6,200,308 B1 | * | 3/2001 | Pope et al. | 606/9 |
| 6,833,551 B2 | * | 12/2004 | Avnery | 250/492.3 |

* cited by examiner

*Primary Examiner*—Krisanne Thornton
(74) *Attorney, Agent, or Firm*—Kusner & Jaffe; Michael A. Centanni

(57) ABSTRACT

A system for irradiating mail, comprising a device for conveying mail along a predetermined path and a device for irradiating the mail moving along the path with a beam of electrons. An apparatus for chilling the mail is provided along the path. The apparatus exposes the mail to a low-temperature, gaseous fluid created using a cryogenic fluid.

15 Claims, 3 Drawing Sheets

SYSTEM AND METHOD FOR DECONTAMINATING ARTICLES

FIELD OF THE INVENTION

The present invention relates to a process for decontaminating articles, and more particularly to a method for decontaminating mail, packages and the like by irradiation, and a method of minimizing scorching and/or degradation of such articles as a result of the irradiation.

BACKGROUND OF THE INVENTION

The recent, purposeful contamination of mail with anthrax spores has resulted in postal services and courier services searching for ways to deactivate any bio-contamination contained on mail or packaging. One effective way to decontaminate anthrax spores and other bio-contaminations is to irradiate the mail with an electron beam (e-beams). One problem associated with the bombardment of mail with e-beams is that it imparts thermal energy to the mail. As a result, the mail heats up during the irradiation process. In some instances, the temperature of the irradiated articles may reach a level where discoloration, and even scorching, of the mail may occur.

The present invention provides a system and method for treating mail so as to minimize scorching and/or degradation of mail during an irradiation process.

SUMMARY OF THE INVENTION

In accordance with a preferred embodiment of the present invention, there is provided a system for irradiating mail, comprising a device for conveying mail along a predetermined path and a device for irradiating the mail moving along the path with a beam of electrons. An apparatus for chilling the mail is provided along the path. The apparatus utilizes a cryogenic fluid and exposes the mail to a low-temperature, gaseous fluid created using the cryogenic fluid.

In accordance with another aspect of the present invention, there is provided a method of irradiating objects, comprising the steps of:

conveying objects along a predetermined path;

exposing the objects to a gaseous fluid formed from a cryogenic fluid; and irradiating the objects on the path.

An advantage of the present invention is a system for decontaminating articles by irradiation.

Another advantage of the present invention is a system as described above that reduces the likelihood of the irradiated articles overheating.

Another advantage of the present invention is a system as described above, wherein the articles to be irradiated are chilled by a cryogenic fluid.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
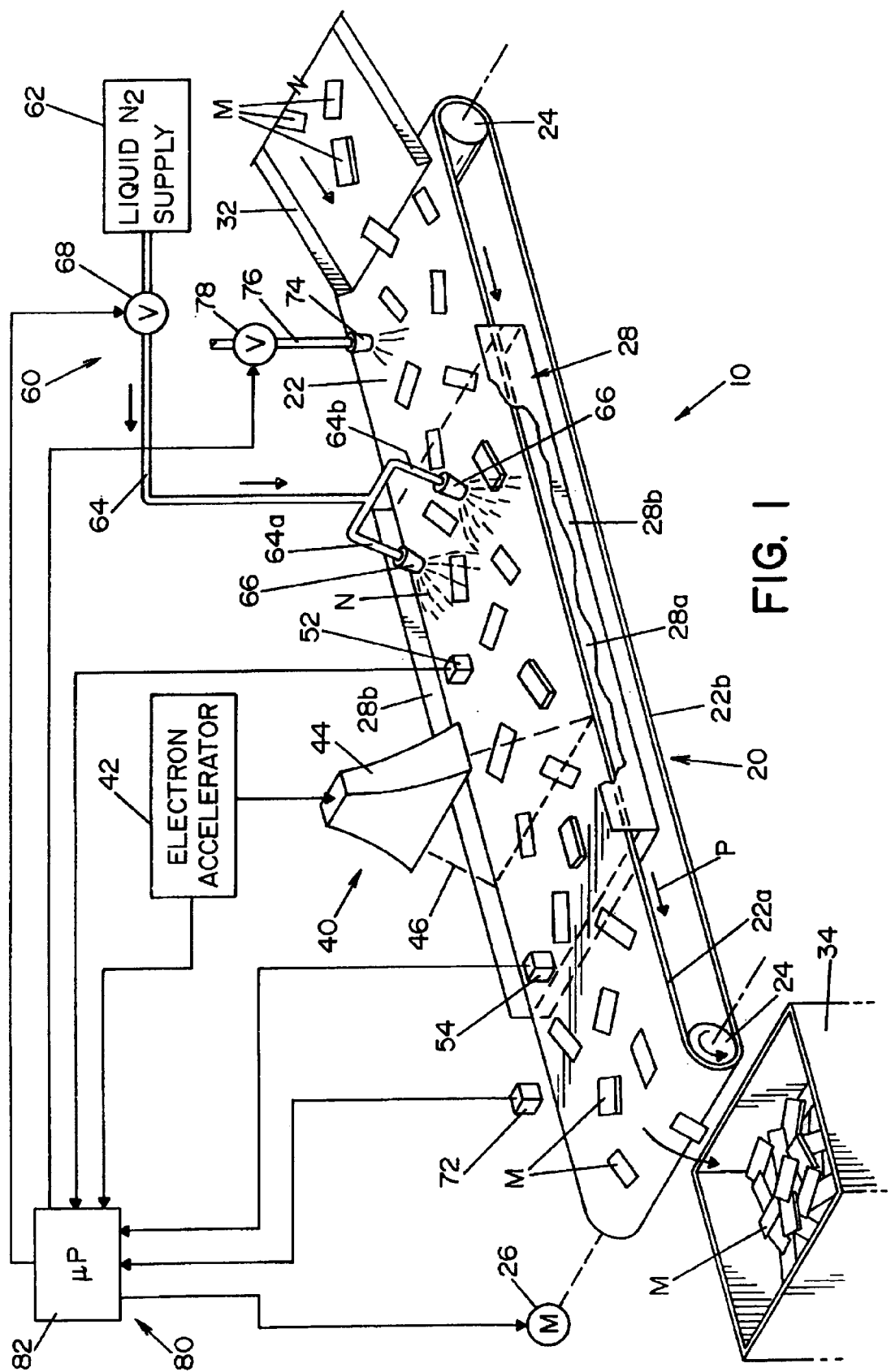
FIG. 1 is a partially pictorial, partially schematic view of a system for decontaminating mail, illustrating a preferred embodiment of the present invention.

Referring now to the drawings wherein the showings are for the purpose of illustrating a preferred embodiment of the invention only, and not for the purpose of limiting same, FIG. 1 shows a system 10 for irradiating mail, in accordance with a preferred embodiment of the present invention. As used herein, the term "mail" refers to envelopes, flyers, catalogs, postcards, magazines, packages and other similar articles typically handled by postal services or by delivery services. In this respect, while the invention shall be described with reference to a system for decontaminating mail, it would be appreciated that the invention may find advantageous application for decontaminating other articles, such as foods, clothing or other similar products.

System 10 includes a conveyor assembly 20 that is essentially comprised of an elongated, endless conveyor belt 22 that travels about two spaced-apart, parallel rollers 24. Belt 22 is preferably formed of an elastomeric material, and includes an upper belt run 22a and a lower belt run 22b. One or both rollers 24 is (are) driven by a variable speed motor 26, as schematically illustrated in FIG. 1.

Figure 3:
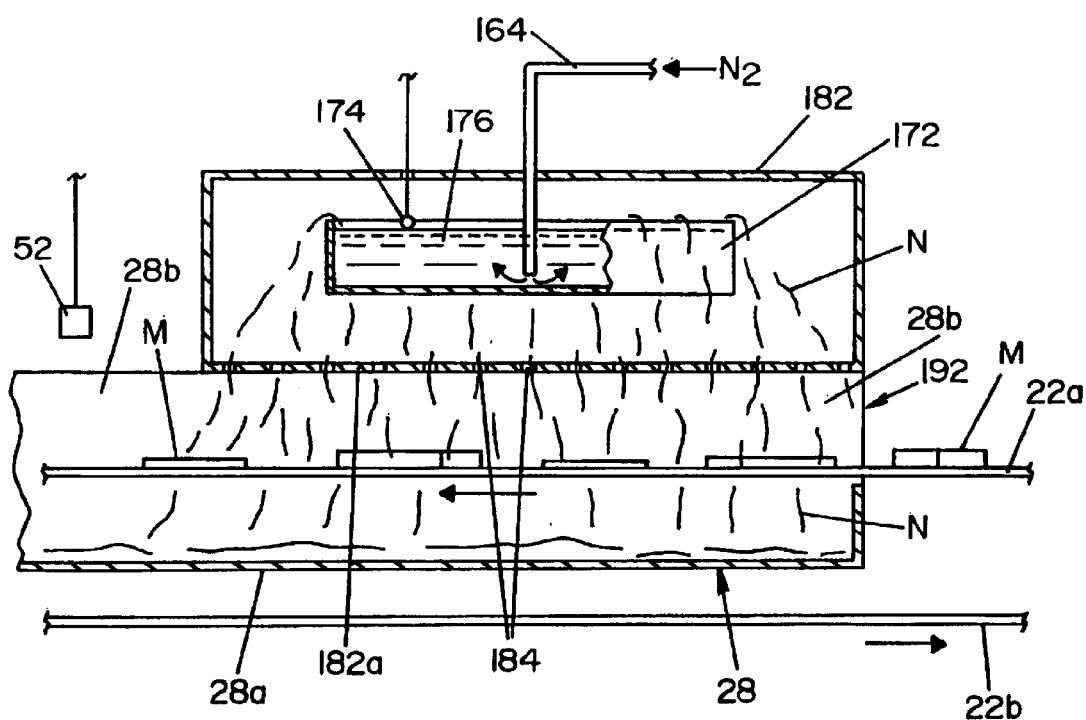
FIG. 3 is a sectional view taken along lines 3—3 of FIG. 2.

At one end of conveyor assembly 20, a chute 32 is provided from which mail, designated "M" in the drawings, is fed onto conveyor belt 22. A collection bin 34 is disposed at the other end of conveyor assembly 20 to receive mail M after it has been conveyed along conveyor belt 22. Upper belt run 22a of conveyor assembly 20 defines a path P along which mail and the like is conveyed An elongated, generally U-shaped trough or channel 28 is disposed beneath upper conveyor belt run 22a. Trough 28 includes a bottom panel 28a and upwardly extending side panels 28b As best seen in FIG. 3, bottom panel 28a is disposed just below upper belt run 22a with side panels 28b extending upwardly adjacent to edges of upper conveyor belt run 22a and above the surface of upper belt run 22a.

Disposed above conveyor assembly 20 is a system 40 for irradiating mail M. In the embodiment shown, system 40 is comprised of an accelerator 42 and a scan horn 44. An electron source (not shown) supplies electrons to accelerator 42 that in turn accelerates the electrons and directs them to horn 44, in a manner that is conventionally known. In a preferred embodiment, electron accelerator 42 is a rotary accelerator with an electron potential capacity of 1 to 10 MeV in integer values Horn 44 is operable to scan the electron beam across conveyor belt 22. The electron beam is schematically illustrated and designated "46" in FIG. 1. Temperature sensors 52, 54 are disposed along path P above conveyor belt 22. Sensors 52, 54 are positioned along conveyor belt 22 such that beam 46 is disposed therebetween. Although a system 40 for applying e-beam irradiation is shown, it will be appreciated by those skilled in the art that mail M may also be irradiated with gamma radiation.

A mail chilling system 60 is disposed along path P. System 60 is comprised of a source 62 of a cryogenic fluid and a conduit 64 for conveying the cryogenic fluid to spray nozzles 66 disposed above the surface of upper conveyor belt run 22a. In the embodiment shown, conduit 64 is split into two channels, 64a, 64b, that are each connected to a spray nozzle 66 Nozzles 66 are preferably formed of a porous, ceramic material as is conventionally known in the art of cryogenic fluids. Nozzles 66 are preferably oriented in the direction of travel of conveyor belt 22, as illustrated in FIG. 1. A valve 68, preferably an electronically controlled valve, is disposed in conduit 64 to control the flow of the cryogenic fluid from source 62 to nozzles 66.

A humidity sensor 72 is disposed in the vicinity of system 10 to detect and monitor the relative humidity of the surrounding environment. A water spray mist head 74 is disposed above upper conveyor run 22a of conveyor belt 22 between shute 32 spray nozzle 66. Spray head 74 is connected to a water line 76 that has an electrically controlled valve 78 disposed therein to control the flow of water to spray head 74. Valve 78 is connected to control system 80, as shown in the drawings, and control system is operable to control valve 78.

A control system 80 is provided to control operations of system 10. Control system 80 is basically a microprocessor 82 that is operable to receive input information from irradiation system 40, temperature sensors 52, 54 and humidity sensors 72, and based upon a program stored therein, to control the speed of motor 26 and the position of valve 68.

Referring now to the operation of system 10, as is conventionally known, irradiating objects with an e-beam will cause an increase in the temperature of the object that is irradiated. System 10 includes an apparatus for chilling an irradiated object to negate the heating effect of an irradiation system 40.

In system 10, mail M is deposited on upper conveyor run 22a of conveyor belt 22 from chute 32. Mail M is preferably separated (by means not shown) so that each piece of mail M to be irradiated is isolated from another so as to insure maximum exposure to e-beam 46. As mail M is conveyed along path P on upper conveyor belt 22a, mail M passes beneath spray nozzles 66. In a preferred embodiment, the cryogenic fluid used in chilling system 60 is nitrogen. Liquid nitrogen is stored in source 62 and conveyed through conduit 64 to spray nozzles 66. Nitrogen N is "sprayed" from nozzles 66, and is essentially vaporized upon exposure to the atmosphere, thereby forming a cloud of nitrogen gas around nozzles 66 and above the surface of upper conveyor belt run 22a. Since nitrogen gas is heavier than air, the cloud of nitrogen gas settles upon mail M as it moves under nozzles 66. The nitrogen gas is extremely cold and as a result, chills and cools mail M moving along upper conveyor belt 22a. Trough or channel 28 essentially confines the nitrogen gas around upper conveyor belt run 22a and around mail M thereon. In this respect, side walls 28b of trough or channel 28 confine the gas much like a liquid flowing through a channel. Thus, the nitrogen gas essentially moves with the upper conveyor belt 22a together with mail M thereon. Temperature sensor 52 monitors the temperature of the mail after it has been chilled by the nitrogen gas. Temperature sensor 52 provides an indication thereof to microprocessor 82.

Mail M is then conveyed past irradiation system 40, wherein mail M has been exposed to e-beam 46. As will be appreciated by those skilled in the art, a certain level of radiation, i.e., dose, is required to deactivate certain bio-contaminations. The dosage of radiation applied to mail M is based upon the energy level of beam 46, as well as the exposure time of mail M to beam 46. Information relating to the speed of conveyor belt 22, as well as the energy output of accelerator 42, are monitored by microprocessor 82. Microprocessor 82 establishes a maximum conveyor velocity above which mail M is not exposed to e-beam 46 for a sufficient period of time so as to receive the desired dose of radiation to kill the bio-contamination(s) thereon.

After mail M passes e-beam 46, the temperature of mail M is detected by temperature sensor 54, and monitored by microprocessor 82 Irradiated mail M is then dropped into collection bin 34, or conveyed by other means not shown to some other location for handling or distribution.

During the operation of system 10, microprocessor 82 monitors temperature sensors 52, 54 and determines the change in temperature of mail M before and after irradiation by e-beam 46. Based upon the determined difference in temperature detected by sensors 52, 54, microprocessor 82 is operable to adjust the modes of operation of system 10. One mode of operation controlled by microprocessor 82 is the amount of cryogenic fluid, i.e., nitrogen, provided to spray nozzles 66. It is desirable that mail M, after irradiation by beam 46, does not exceed a certain predetermined, set target temperature. If the temperature sensed by temperature sensor 54 is above the desired set target temperature, microprocessor 82 is operable to move valve 68 to allow more nitrogen to be sprayed by nozzles 66 thereby providing more cooling or chilling of the mail prior to irradiation. In another embodiment, liquid nitrogen could be sprayed directly on the mail to effect maximum cooling.

Another mode of operation controlled by microprocessor 82 is the speed of conveyor belt 22. As indicated above, a maximum speed is established by the necessary dosage of radiation the mail must receive. Exceeding this speed would mean that the mail is not exposed to e-beam 46 for a sufficient amount of time to reach the desired dosage. With this maximum speed established, microprocessor 82 may control the speed of conveyor belt 22, at any speed below this maximum speed in conjunction with the sensed temperature of mail M after irradiation to establish a conveyor speed that optimizes the irradiation process, yet minimizes overheating of mail M. As will be appreciated, microprocessor 82 is operable to control both the conveyor speed and the flow of nitrogen to nozzles 66 to provide optimum operation of system 10.

In accordance with another aspect of the present invention, microprocessor 82 monitors the relative humidity of the atmosphere around system 10. In this respect and in accordance with one aspect of the present invention, it is preferable that system 10 operates at a predetermined relative humidity between about 30% and 70%. A relative humidity within this range is preferred in that the chilling or cooling of mail M is easier if the moisture content of the paper or wrapping thereof is at or above a desired level. The liquid nitrogen essentially freezes the moisture molecules on and/or within an envelope or packaging. Upon irradiation by e-beam 46, a certain level of energy is required to melt the frozen water crystals within the paper or packaging, and then to vaporize the water molecules. Such transformation requires a significant amount of energy thereby reducing the heating effect on mail M. Control system 80 is operable to monitor the temperature difference of mail M before and after irradiation and to monitor the relative humidity of the surrounding environment. In response thereto, control system 80 controls valve 78 to allow mail M to be "misted" with water, prior to exposure to the liquid nitrogen. Misting mail M and conveyor belt 22 enhances the cooling effect of the liquid nitrogen, as indicated above.

In one respect, trough or channel 28 beneath upper conveyor belt run 22a basically confines and maintains the nitrogen gas therein, and thereby chilling not only mail M, but also conveyor belt 22 as well as trough or channel 28 itself. This cooling affect further reduces the heating effect of e-beam 46 on mail M, conveyor belt 22 and trough or channel 28

Figure 2:
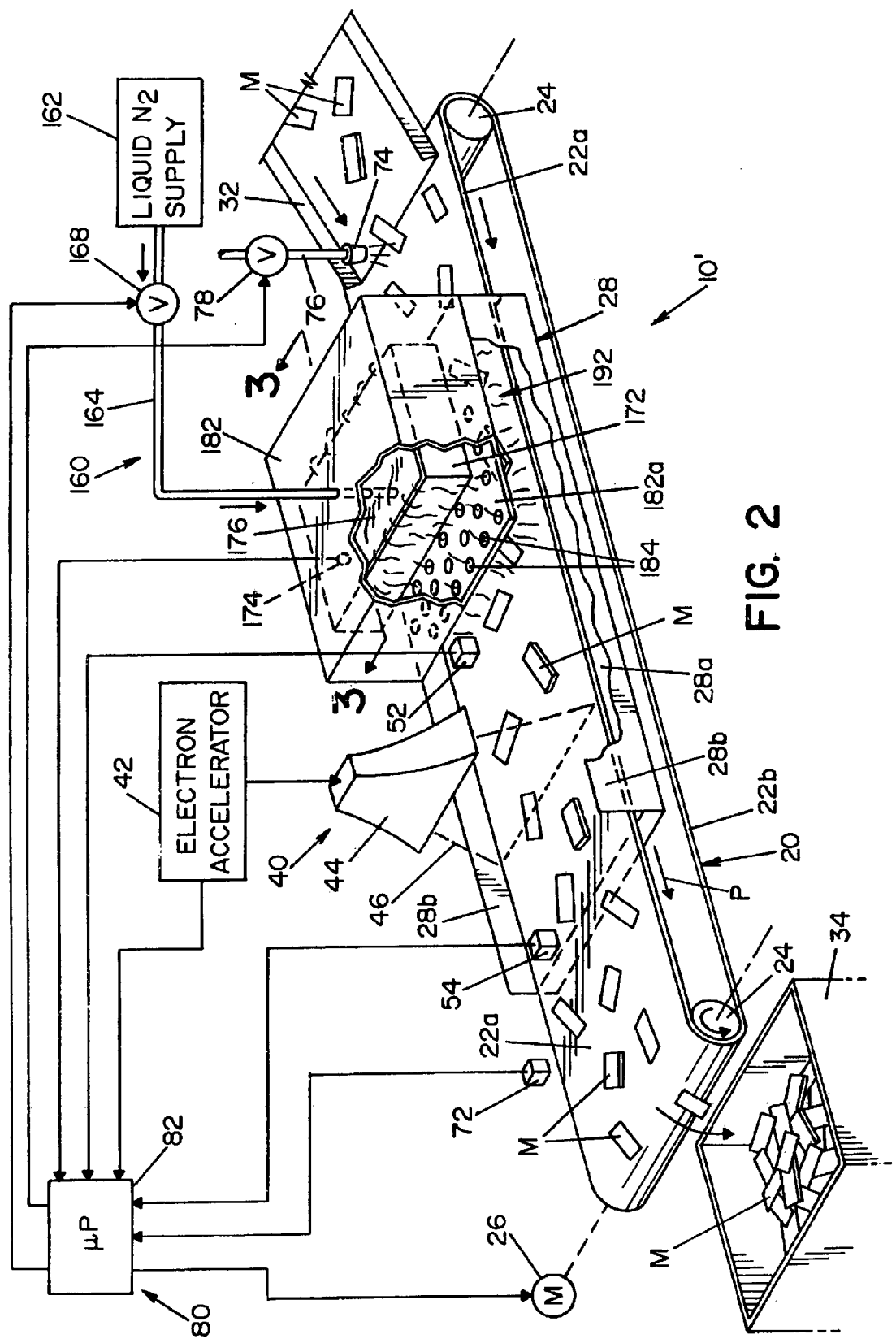
FIG. 2 is a partially pictorial, partially schematic view of a process for decontaminating mail, illustrating another embodiment of the present invention.

Referring now to FIGS. 2 and 3, a system 10', illustrating another embodiment of the present invention, is shown. System 10' is similar in many respects to system 10, and therefore like components are identified by like reference numbers In system 10', mail chilling system 60 is replaced by a mail chilling system 160

Mail chilling system 160 is comprised of a supply 162 of a cryogenic fluid. A conduit 164 connects supply 162 with a holding tank 172 that is designed to receive the cryogenic fluid. A level sensor 174 is provided within holding tank 172 to provide an indication of the level of the cryogenic fluid therein.

A housing 182 surrounds and encloses holding tank 172. Conduit 164 extends through housing 182 into holding tank 172. As illustrated in FIG. 3, holding tank 172 is essentially disposed within housing 182 such that holding tank 172 is spaced from housing 182. In the embodiment shown, both holding tank 172 and housing 182 are generally rectangular in shape Housing 182 includes a lower housing wall 182a having a plurality of apertures 184 formed therein Apertures 184 may have any configuration, but in the embodiment shown, are circular. Apertures 184 preferably have predetermined and uniform designs, and are preferably arranged in a uniform pattern.

Housing 182 is dimensioned to have a width approximately equal to the width of trough or channel 28. Housing 182 is positioned to engage side walls 28a of trough 28, wherein a tunnel or chamber 192 is formed between housing 182 and trough 28. Upper belt run 22a of conveyor belt 22 passes through tunnel or chamber 192. Apertures 184 of housing 182 are positioned to be within tunnel 192 and to be spaced above upper belt run 22a.

Referring now to the operation of system 10', like system 10, system 10' is adapted to chill mail M during an irradiation process. System 10' is adapted for use with a cryogenic fluid, such as nitrogen, that is heavier than air. Microprocessor 82 controls valve 168 to allow nitrogen from supply tank 162 to fill holding tank 172 to form a pool 176 of liquid nitrogen therein. Level sensor 174 provides microprocessor 82 with an indication of the level of nitrogen within holding tank 172. Microprocessor 82 controls the position of valve 168 in conduit 164 in response to signals from level sensor 174 to maintain the supply of nitrogen from conduit 164 at a desired rate to maintain a desired level in holding tank 172

The nitrogen in holding tank 172, when exposed to air, vaporizes Since nitrogen is heavier than air, the nitrogen vapor fills the bottom of housing 182. Gravity alone will cause the heavier nitrogen vapor to permeate through apertures 184 and the bottom of housing wall 182a. However, since housing 172 is essentially sealed, the nitrogen gas within housing 182 builds up an internal vapor pressure which although small, is sufficient to force the nitrogen gas through apertures 184 in bottom housing wall 182a. Apertures 184 are preferably dimensioned to result in the nitrogen vapor gas being forced through apertures 184 into tunnel 192. The nitrogen vapor exiting housing 182 accumulates within tunnel 192. Mail M passing through tunnel 192 is exposed to the nitrogen vapor in a generally closed chamber, i.e., in the space between housing 182 and trough or channel 28. Mail M is exposed to the chilling effect of the nitrogen vapor for the time period it takes for mail M to be conveyed through tunnel or chamber 192.

As with the prior embodiment, sensors 52, 54 can monitor the temperature of mail M before and after e-beam 46. With such information, microprocessor 82 may modify the speed of conveyor belt 22 to increase or decrease the cooling period within tunnel 192. In the alternative, the flow of nitrogen to holding tank 172 may be increased or decreased to increase or decrease the amount of nitrogen vapor within tunnel or chamber 192.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

We claim:

1. A system for irradiating mail, comprising:
    a device for conveying mail along a predetermined path;
    a device for irradiating mail moving along said path with a beam of electrons; and
    an apparatus for chilling the mail moving along said path with a cryogenic fluid, said apparatus for chilling exposing said mail to a low-temperature, cryogenic fluid.

2. A system for irradiating mail as defined in claim 1, wherein said apparatus for chilling comprises at least one sprayer for spraying said cryogenic fluid onto said mail.

3. A system for irradiating mail as defined in claim 1, wherein said mail is conveyed through a chamber containing a gaseous fluid in said chamber.

4. A system for irradiating mail as defined in claims 2 or 3, wherein said system further includes:
    a first temperature sensor for sensing the temperature of said mail before an exposure to said device for irradiating, and a second temperature sensor for sensing the temperature of the mail after said exposure to said device for irradiating; and
    controlling means for varying a mode of operation of said system in response to a difference in a temperature sensed by said first temperature sensor and a temperature sensed by said second temperature sensor.

5. A system for irradiating mail as defined in claim 4, wherein one mode of operation is to vary the speed of said device for conveying.

6. A system for irradiating mail as defined in claim 4, wherein one mode of operation is to vary the amount of cryogenic fluid exposed to said mail.

7. A system for irradiating mail as defined in claim 1, wherein said cryogenic fluid is nitrogen.

8. A system for irradiating mail as defined in claim 3, wherein said apparatus for chilling is comprised of a housing disposed along said path, said housing containing a cryogenic vapor and having openings oriented toward said path.

9. A method of irradiating objects, comprising the steps of:
    conveying objects along a predetermined path;
    exposing said objects to a gaseous fluid formed from a cryogenic fluid; and
    irradiating said objects on said path.

10. A method as defined in claim 9, further comprising the steps of:
    sensing the temperature of objects after they are irradiated;
    comparing a sensed temperature of said objects to a set temperature value; and conveying said objects at a different speed along said path if said sensed temperature value is different from said set temperature value.

11. A method as defined in claim 10, wherein said object is conveyed at a higher speed along said path if said sensed temperature is greater than said set temperature value.

12. A method as defined in claim 9, further comprising the steps of:

sensing the temperature of objects after they are irradiated;

comparing a sensed temperature of said objects to a set temperature value; and exposing said object to a different amount of said gaseous fluid if said sensed temperature is different from said set temperature value.

13. A method as defined in claim 12, wherein said object is exposed to more of said gaseous fluid if said sensed temperature is greater than a set temperature.

14. A method as defined in claim 9, wherein said irradiation is comprised of x-ray irradiation.

15. A method as defined in claim 9, wherein said irradiation is comprised of gamma ray irradiation.

* * * * *